(12) United States Patent
Echigo et al.

(10) Patent No.: US 7,473,806 B2
(45) Date of Patent: Jan. 6, 2009

(54) MODIFIED CHAIN ALIPHATIC POLYAMINE

(75) Inventors: Masatoshi Echigo, Kanagawa (JP); Hisayuki Kuwahara, Kanagawa (JP); Takeshi Koyama, Kanagawa (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 10/739,006

(22) Filed: Dec. 19, 2003

(65) Prior Publication Data

US 2004/0171791 A1 Sep. 2, 2004

(30) Foreign Application Priority Data

| Dec. 26, 2002 | (JP) | ............................. 2002-377729 |
| Apr. 23, 2003 | (JP) | ............................. 2003-118064 |

(51) Int. Cl.
*C07C 211/00* (2006.01)

(52) U.S. Cl. .................................................. 564/509
(58) Field of Classification Search .................. 564/509
See application file for complete search history.

(56) References Cited

U.S. PATENT DOCUMENTS

| 3,376,344 A | * | 4/1968 | Lane et al. |
| 4,034,040 A | | 7/1977 | Cronin et al. |
| 4,182,849 A | | 1/1980 | Ezzell |
| 2002/0055605 A1 | | 5/2002 | Yonehama et al. |

FOREIGN PATENT DOCUMENTS

| CH | 503 068 | 3/1971 |
| DE | 14 44 278 | 12/1968 |
| GB | 788 915 | 1/1958 |

OTHER PUBLICATIONS

Database CAPLUS on STN, Acc. No. 1933:10106, Munch et al, DE 561156 (Dec. 19, 1930) (abstract).*
Database CAPLUS on STN, Acc. No. 1968:506661, Nakajima et al., Nippon Kagaku Zasshi (1968), 89(4), p. 408-411 (abstract).*
Database CAPLUS on STN, Acc. No. 1948:31920, Braz et al., Doklady Akademii Nauk SSSR (1948), 59, p. 489-492 (abstract).*
Database CAPLUS on STN, Acc. No. 1966:438062, Gelbard et al., Comptes Rendus des Seances de l'Academie des Sciences, Serie C: Sciences Chimiques (1966), 262(22), p. 1587-90 (abstract).*
Database CAPLUS on STN, Acc. No. 1957:44350, Reiff, Acta Tropica (1956), 13, p. 289-318 (abstract).*
Rehse et al., Archiv der Pharmazie (1990), 323(5), p. 287-294.*
Database Crossfire Beilstein 'Online! Beilstein Institut zur Förderung der Chemischen Wissenschaften, Frankfurt am Main, DE; Database accession No. 7477320 (BRN), Nov. 1996, XP002276258.
Database Crossfire Beilstein 'Online! Beilstein Institut zur Förderung der Chemischen Wissenschaften, Frankfurt am Main, DE; Database accession No. 3052585 (BRN), Jul. 1989, XP002276259.
Database Crossfire Beilstein 'Online! Beilstein Institut zur Förderung der Chemischen Wissenschaften, Frankfurt am Main, DE; Database accession No. 2373058 (BRN), Jul. 1989, XP002276260.
Database Crossfire Beilstein 'Online! Beilstein Institut zur Förderung der Chemischen Wissenschaften, Frankfurt am Main, DE; Database accession No. 4876588 (BRN), May 1993, XP002276261.
Database Crossfire Beilstein 'Online! Beilstein Institut zur Förderung der Chemischen Wissenschaften, Frankfurt am Main, DE; Database accession No. 1783156 (BRN), Feb. 1989, XP002276263.
Maeda, Mizuo et al: "Synthesis of new monomers having a primary amino group by lithium alkylamide catalyzed addition reaction of N-alkylethylenediamines with 1, 4-divinylbenzene" Makromolekulare Chemie (1980), 181(11), 2251-7, XP009028926.
Database Crossfire Beilstein, Beilstein Registry No. 2142004, 1989.
Database Crossfire Beilstein, Beilstein Registry No. 2228312, 1989.

* cited by examiner

*Primary Examiner*—Brian J Davis
(74) *Attorney, Agent, or Firm*—Wenderoth, Lind & Ponack, L.L.P.

(57) ABSTRACT

A modified chain aliphatic polyamine obtained by addition reaction of a chain aliphatic polyamine having a specific structure and an unsaturated hydrocarbon compound has a low viscosity and it provides, when used as a curing agent for epoxy resin, an epoxy resin composition which can provide an epoxy resin cured product having an excellent property. Further, a modified chain aliphatic polyamine composition obtained by addition reaction of a chain aliphatic polyamine having a specific structure and an unsaturated hydrocarbon compound followed by the removing step of unreacted chain aliphatic polyamine to reduce its amount less than 2% by weight provides, when used as a curing agent for epoxy resin, an epoxy resin composition which can provide an epoxy resin cured product having an excellent property.

9 Claims, 3 Drawing Sheets

MODIFIED CHAIN ALIPHATIC POLYAMINE

BACKGROUND OF THE INVENTION

1. Field of the Invention

The present invention relates to a modified chain aliphatic polyamine and a composition containing the same. The present invention also relates to a curing agent for epoxy resin comprising said modified chain aliphatic polyamine, an epoxy resin composition comprising said curing agent for epoxy resin, and an epoxy resin cured product obtained by curing said epoxy resin composition. In the present invention, the term "chain aliphatic" includes an acyclic aliphatic compound.

The modified chain aliphatic polyamine is applicable to a curing agent for epoxy resin and a raw material thereof to be utilized in an extremely wide field including application to a coating material, a material for electricity and electronics, a civil engineering and construction material, an adhesive, and a composite material; and is applicable to a chain extender and a raw material thereof of a polyurethane resin to be utilized in a very wide field including clothes, sports equipments, home appliances, electronics, medical apparatuses, motor cars, transporting apparatuses, civil engineering and construction materials and industrial materials as a foam, an elastomer, a coating, an adhesive, a binder, fibers, a leather, a flooring material, a water proof material, an athletic material, a sealant, a coking, a medical material and a fiber treating agent. Furthermore, it can be utilized widely in various field such as a paper reinforcing agent, chemicals for rubber, boiler compounds, a slag inhibitor, a surfactant, an emulsifier, a dye, a pigment, a dyeing assistant, an oil solution for fiber, cosmetics, a crease-proofing agent, a chelating agent, a ore floatation agent, a detergent, a thixotropic agent, a pH adjuster, a pesticide, a herbicide, a stabilizer for agricultural chemicals, feed additives, catalysts, a polymerization accelerator, a polymerization inhibitor, a stabilizer, an ion-exchange resin, a gas absorbent, an antioxidant, a corrosion inhibitor, an antirust, a sterilizer, an antibacterial agent, an antifreeze liquid, a lubrication oil, a lubricant, an intermediate of pharmaceuticals, polyamide, a solvent and photographic chemicals.

2. Related Art

It has widely been known that various polyamines are used as a curing agent for epoxy resin and a raw material for curing agent thereof or a chain extender for polyurethane resin and a raw material for chain extender thereof.

However, these polyamines are scarcely used as it is as a curing agent for epoxy resin. In most cases, they are used after various modifications suitable for their own characteristics caused by the reactivity of their amino groups, namely active hydrogen atoms that each polyamine has, depending on the intended purpose such as improving in safety and hygiene, improving in workability and providing of adequate property of cured products suitable for their own application.

For example, Japanese Patent Kokai (Laid-open) No. 2002-161076 describes that a curing agent for epoxy resin obtained by modifying metaxylylenediamine and the like provides an epoxy resin composition having a long pot life.

Representative methods for a modification of polyamines include 1) a modification by Mannich reaction with a phenol compound and an aldehyde compound, 2) a modification by reaction with an epoxy compound, 3) a modification by reaction with a compound having a carboxyl group, 4) a modification by Michael reaction with an acryl compound and 5) combinations of any of 1) to 4).

In general, the molar number of modification of polyamine is selected from the range wherein the obtainable modified polyamine has at least one active hydrogen atom derived from the amino groups in the polyamine before modification.

When the molar number of modification is relatively low, the obtainable modified polyamine has a low viscosity. However, the amount of unreacted polyamine becomes large, which causes such defects that the obtainable modified polyamine may have high toxicity and skin irritativeness may remain. Moreover, the epoxy resin composition using the modified polyamine as a curing agent for epoxy resin may have such defects that the appearance of a coating film tends to be inferior by the phenomena of whitening or tackiness because such epoxy resin composition easily produces carbamate or carbonate by absorbing carbon dioxide or water vapor in the atmosphere.

On the other hand, when the molar number of modification is relatively high, the content of unreacted polyamine in the obtainable modified polyamine is small. However, the viscosity of the modified polyamine becomes high, which brings about the requirement of lowering the viscosity by adding solvents or diluents in order to improve workability.

It is desired not to use solvents because of environmental problems and to limit the amount of diluents added in order to avoid the deterioration of the properties of cured products.

SUMMARY OF THE INVENTION

An object of the present invention is to provide a modified polyamine having a low viscosity which provides, when used as a curing agent for epoxy resin, an epoxy resin composition that can provide an epoxy resin cured product with excellent properties.

As a result of extensive studies, the inventors have found that a modified chain aliphatic polyamine having a particular structure has a low viscosity and a relatively small content of unreacted aliphatic polyamine even if lowering the molar number of modification in the process of producing the same, and an epoxy resin composition containing a curing agent for epoxy resin comprising the above modified chain aliphatic polyamine provides an epoxy resin cured product having excellent properties, and have accomplished the present invention.

Further, the inventors have found that a modified chain aliphatic polyamine composition obtainable by addition reaction of a chain aliphatic polyamine having a particular structure and an unsaturated hydrocarbon compound wherein the content of the unreacted chain aliphatic polyamine is less than a certain amount provides, when used as a curing agent for epoxy resin, an epoxy resin composition which can provide an epoxy resin cured product having excellent properties such as an excellent appearance of a coating film, an excellent water resistance and an excellent chemical resistance, and have accomplished the present invention.

Especially, the inventors have found that a modified chain aliphatic polyamine having a particular structure obtainable by addition reaction of diethylenetriamine and styrene under strong base catalyst has a low viscosity and the content of unreacted diethylenetriamine is relatively low, and therefore a curing agent for epoxy resin comprising said modified chain aliphatic polyamine can provide an epoxy resin cured product having excellent properties, and have accomplished the present invention.

Therefore, the present invention provides a modified chain aliphatic polyamine described in the following 1) to 5), a modified chain aliphatic polyamine composition described in 6) to 12), a curing agent for epoxy resin described in 13), an epoxy resin composition described in 14), and an epoxy resin cured product described in 15).

1) A modified chain aliphatic polyamine represented by the following formula (1).

R1R2N—(CH$_2$CH$_2$NR3)$_n$—CH$_2$CH$_2$NR4R5     (1)

wherein each of substituents R1, R2, R3, R4 and R5 represents independently a hydrogen atom or an unsaturated hydrocarbon group having a carbon number of 2 to 16, at least one of which is an unsaturated hydrocarbon group having a carbon number of 2 to 16, and "n" represents a number of 0 to 4.

2) The modified chain aliphatic polyamine according to 1), wherein said "n" is 1 or 2 and said unsaturated hydrocarbon group is a phenethyl group in said formula (1).

3) The modified chain aliphatic polyamine according to 1), wherein "n" is 1 and said unsaturated hydrocarbon group is a phenethyl group in said formula (1).

4) The modified chain aliphatic polyamine according to 1) to 3), wherein 1 to 3 substituents out of said substituents R1, R2, R3, R4 and R5 is/are an unsaturated hydrocarbon group.

5) The modified chain aliphatic polyamine according to 1) to 4), which is an addition product obtainable by addition reaction of a chain aliphatic polyamine represented by the following formula (2) and an unsaturated hydrocarbon compound selected from the group consisting of a chain unsaturated hydrocarbon compound, an alicyclic unsaturated hydrocarbon compound and an aromatic unsaturated hydrocarbon compound having a carbon number of 2 to 16.

H$_2$N—(CH$_2$CH$_2$NH)$_n$—CH$_2$CH$_2$NH$_2$     (2)

wherein "n" represents a number of 0 to 4.

6) A modified chain aliphatic polyamine composition comprising a modified chain aliphatic polyamine obtainable by addition reaction of a chain aliphatic polyamine represented by the following formula (2) and an unsaturated hydrocarbon compound selected from the group consisting of a chain unsaturated hydrocarbon compound, an alicyclic unsaturated hydrocarbon compound and an aromatic unsaturated hydrocarbon compound having a carbon number of 2 to 16.

H$_2$N—(CH$_2$CH$_2$NH)$_n$—CH$_2$CH$_2$NH$_2$     (2)

wherein "n" represents a number of 0 to 4.

7) The modified chain aliphatic polyamine composition according to 6), wherein said chain aliphatic polyamine is diethylenetriamine and/or triethylenetetramine.

8) The modified chain aliphatic polyamine composition according to 6) or 7), wherein said unsaturated hydrocarbon compound is at least one selected from the group consisting of ethylene, propylene, butene, butadiene, pentene, hexene, heptene, octene, nonene, decene, isobutylene, 2-pentene, 3-methyl-1-butene, 2-methyl-2-butene, 2,3-dimethyl-2-butene, cyclohexene, cyclohexadiene, styrene and divinylbenzene.

9) The modified chain aliphatic polyamine composition according to 6) to 8), wherein said unsaturated hydrocarbon compound is styrene.

10) The modified chain aliphatic polyamine composition according to 6) to 9), wherein a molar number of modification of said chain aliphatic polyamine by said unsaturated hydrocarbon compound satisfies the following mathematical formula (1).

$$\frac{A}{40} \leq X < A \quad (1)$$

wherein "A" represents a number of active hydrogen atoms in said chain aliphatic polyamine and "X" represents a molar number of modification.

11) The modified chain aliphatic polyamine composition according to 6) to 10), wherein the content of unreacted chain aliphatic polyamine is less than 2% by weight based upon the total weight of said modified chain aliphatic polyamine composition.

12) The modified chain aliphatic polyamine composition according to 6), which comprises the modified chain aliphatic polyamine according to 1) to 5).

13) A curing agent for epoxy resin comprising the modified chain aliphatic polyamine according to 1) or the modified chain aliphatic polyamine composition according to 6).

14) An epoxy resin composition comprising epoxy resin and the curing agent for epoxy resin according to 13).

15) An epoxy resin cured product obtained by curing the epoxy resin composition according to 14).

That is, the present invention provides the following inventions (I) and (II);

(I) The present invention (I) relates to a modified chain aliphatic polyamine represented by the following formula (1), a curing agent for epoxy resin comprising said modified chain aliphatic polyamine, an epoxy resin composition comprising said curing agent for epoxy resin and an epoxy resin cured product obtained by curing said epoxy resin composition.

R1R2N—(CH$_2$CH$_2$NR3)$_n$—CH$_2$CH$_2$NR4R5     (1)

wherein each of substituents R1, R2, R3, R4 and R5 represents independently a hydrogen atom or an unsaturated hydrocarbon group having a carbon number of 2 to 16, at least one of which is an unsaturated hydrocarbon group having a carbon number of 2 to 16, and "n" represents a number of 0 to 4.

(II) The present invention (II) relates to a modified chain aliphatic polyamine composition obtainable by addition reaction of a chain aliphatic polyamine represented by the following formula (2) and an unsaturated hydrocarbon compound selected from the group consisting of a chain unsaturated hydrocarbon compound, an alicyclic unsaturated hydrocarbon compound and an aromatic unsaturated hydrocarbon compound having a carbon number of 2 to 16.

H$_2$N—(CH$_2$CH$_2$NH)$_n$—CH$_2$CH$_2$NH$_2$     (2)

wherein "n" represents a number of 0 to 4.

DETAILED DESCRIPTION OF THE INVENTION

Figure 1:
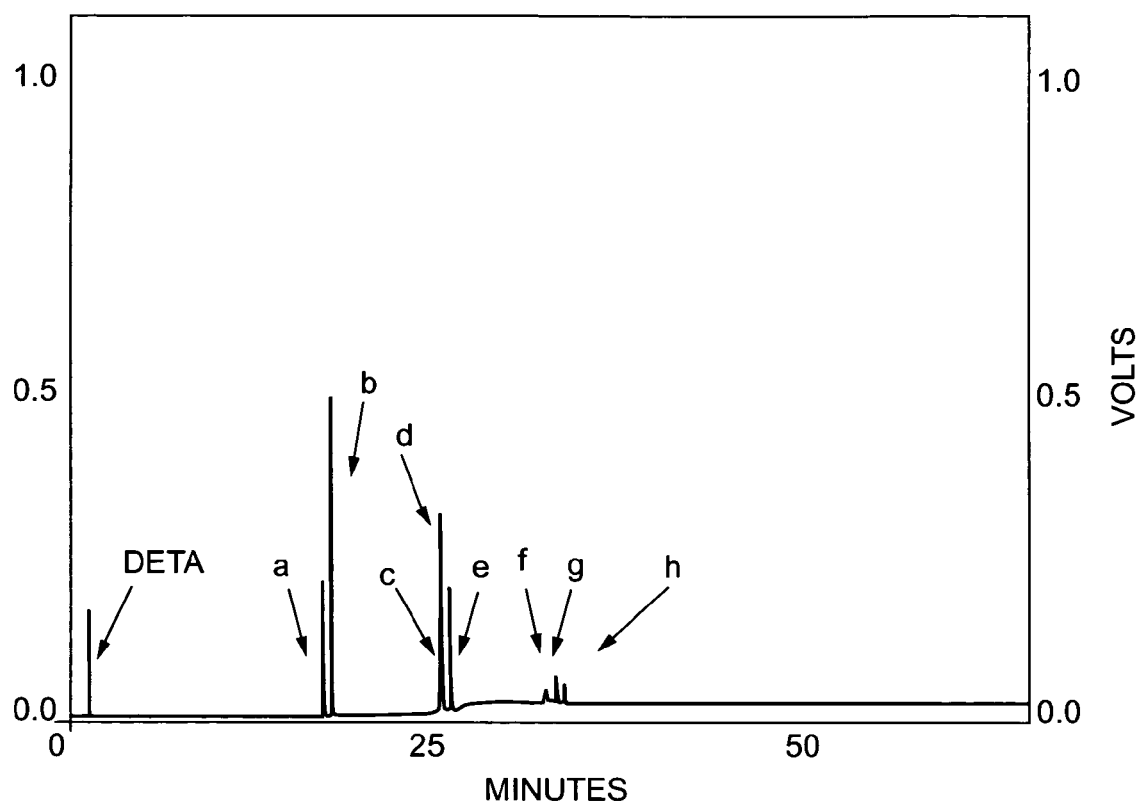
FIG. 1 is a GC chromatogram of polyamine(1) synthesized in Example 1.

The modified chain aliphatic polyamine of the present invention is a new chemical compound represented by the following formula (1).

R1R2N—(CH₂CH₂NR3)ₙ—CH₂CH₂NR4R5     (1)

In the above formula (1), the substituents R1, R2, R3, R4 and R5 represent, each independently, a hydrogen atom or an unsaturated hydrocarbon group having a carbon number of 2 to 16. At least one of the substituents is an unsaturated hydrocarbon group having a carbon number of 2 to 16. The more preferable carbon number of the unsaturated hydrocarbon group is 2 to 10.

"n" in the formula (1) represents an integer number of 0 to 4, preferably 1 or 2.

The modified chain aliphatic polyamine of the present invention (I) having the above-mentioned structure has a relatively low viscosity. Moreover, when it is produced by the process to be described hereinafter, the content of unreacted chain aliphatic polyamine is relatively low even if lowering the molar number of modification. Thus, such modified chain aliphatic polyamine can provide, when used as a curing agent for epoxy resin, an epoxy resin cured product having excellent properties.

In the formula (1), the most preferable number of integer "n" is 1. That is, the most preferable compound of the above modified chain aliphatic polyamine is a compound represented by the formula (3).

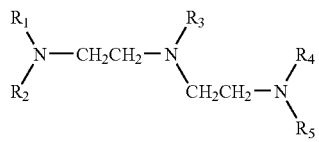
(3)

As with the formula (1), the substituents R1, R2, R3, R4 and R5 in the formula (3) represents, each independently, a hydrogen atom or an unsaturated hydrocarbon group having a carbon number of 2 to 16, at least one of which is an unsaturated hydrocarbon group having a carbon number of 2 to 16. The more preferable carbon number of the unsaturated hydrocarbon group is 2 to 10. The most preferable example of the unsaturated hydrocarbon group is a phenethyl group.

Further, it is preferable that 1 to 3 substituent(s) out of said substituents R1, R2, R3, R4 and R5 is/are an unsaturated hydrocarbon group, and it is more preferable that said 1 to 3 substituent(s) is/are a phenethyl group.

Examples of preferable modified chain aliphatic polyamines of the present invention (I) wherein 1 to 3 substituent(s) out of said substituents R1, R2, R3, R4 and R5 is/are a phenethyl group are shown as the following compounds (a) to (h);

(i) Examples of compounds wherein one of the substituents R1 to R5 is a phenethyl group:

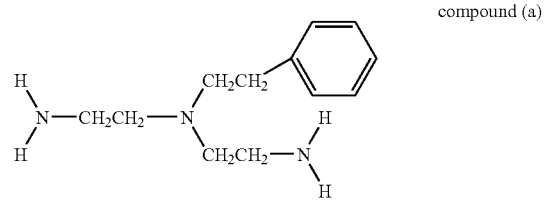
compound (a)

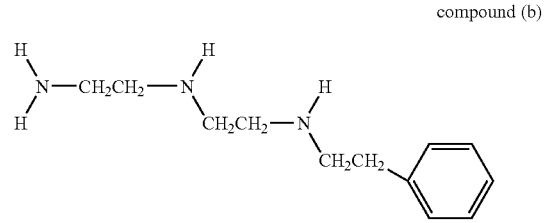
compound (b)

(ii) Examples of compounds wherein two of the substituents R1 to R5 are a phenethyl group:

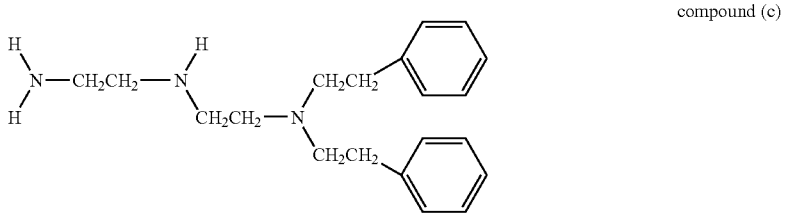
compound (c)

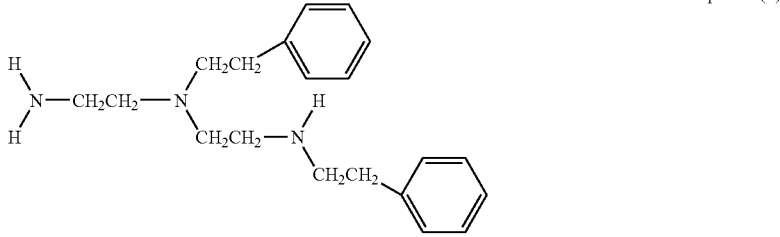
compound (d)

-continued

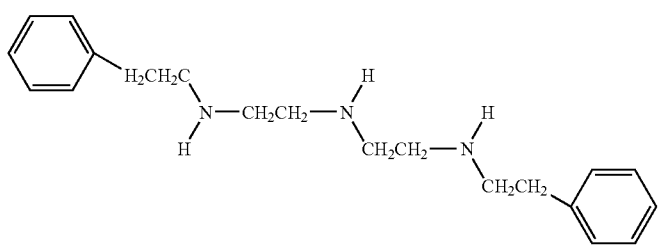
compound (e)

(iii) Examples of compounds wherein three of the substituents R1 to R5 are a phenethyl group:

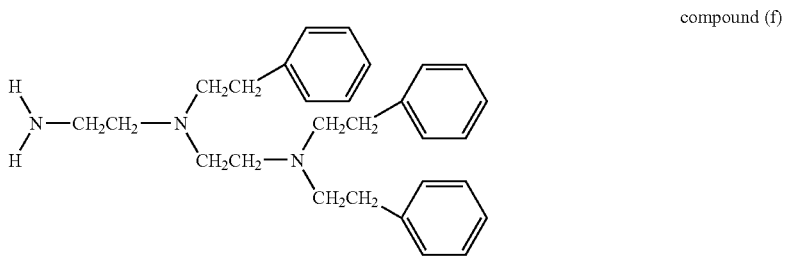
compound (f)

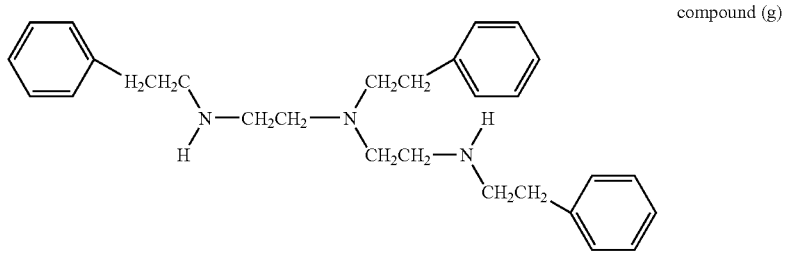
compound (g)

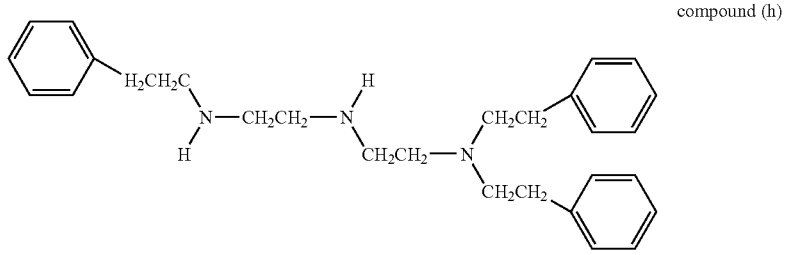
compound (h)

The modified chain aliphatic polyamine of the present invention (I) is, preferably, obtainable by the method comprising the step of addition reaction of a chain aliphatic polyamine represented by the formula (2) and an unsaturated hydrocarbon compound selected from the group consisting of a chain unsaturated hydrocarbon compound, an alicyclic unsaturated hydrocarbon compound and an aromatic unsaturated hydrocarbon compound having a carbon number of 2 to 16, preferably 2 to 10.

$$H_2N-(CH_2CH_2NH)_n-CH_2CH_2NH_2 \quad (2)$$

wherein "n" represents a number of 0 to 4, preferably 1 to 2.

Examples of the chain aliphatic polyamine to be used in the present invention include ethylenediamine, diethylenetriamine, triethylenetetramine, tetraethylenepentamine and pentaethylenehexamine, among which diethylenetriamine and triethylenetetramine are particularly preferable.

The unsaturated hydrocarbon compound to be used in the present invention has a carbon number of 2 to 16, preferably 2 to 10.

Among said unsaturated hydrocarbon compound, examples of the chain unsaturated hydrocarbon compound to be used in the present invention include an alkenyl compound and an alkadienyl compound such as ethylene, propylene, butene, butadiene, pentene, hexene, heptene, octene, nonene, decene, isobutylene, 2-pentene, 3-methyl-1-butene, 2-methyl-2-butene and 2,3-dimethyl-2-butene. Examples of an alicyclic unsaturated hydrocarbon compound include a cycloalkenyl compound such as cyclohexene and a cycloalkadienyl compound such as cyclohexadiene. Examples of an aromatic unsaturated hydrocarbon compound include styrene and divinylbenzene. Among these unsaturated hydrocarbon compounds, styrene is particularly preferable.

The most preferable compound of the modified chain aliphatic polyamine of the present invention (I), namely a modified chain aliphatic polyamine represented by the above formula (1) wherein n=1 and the substituents R1 to R5 are a hydrogen atom or a phenethyl group each independently, is a product obtained by addition reaction of diethylenetriamine and styrene.

As mentioned above, the modified chain aliphatic polyamine of the present invention (I) is preferably an addition product obtainable by addition reaction of a chain aliphatic polyamine having a particular structure and an unsaturated hydrocarbon compound, and it can be extracted appropriately by a well known method from the reaction product after addition reaction.

The viscosity of the modified chain aliphatic polyamine of the present invention (I) is preferably 10 to 1000 mPa·s/23 °C. When the viscosity is larger than 1000 mPa·s, its workability as a curing agent for epoxy resin may be deteriorated.

The modified chain aliphatic polyamine of the present invention (I) has reactivity with epoxy resin and isocyanate or the like, and is useful for a curing agent for epoxy resin or a chain extender for polyurethane resin.

When a modified chain aliphatic polyamine of the present invention (I), especially a modified chain aliphatic polyamine obtained by addition reaction of diethylenetriamine and styrene is used as a curing agent for epoxy resin, it may be used independently or may be used by mixing together with other polyamine-type curing agents for epoxy resin.

In the case of using as a mixture with other curing agents, the mixing ratio of the modified chain aliphatic polyamine is preferably 20% by weight or more, more preferably 30% by weight or more based upon the total weight of the curing agent for epoxy resin. When the mixing ratio of the modified chain aliphatic polyamine is less than 20% by weight, it may cause the deterioration of the property of the epoxy resin cured product obtainable by using the curing agent for epoxy resin comprising the modified chain aliphatic polyamine of the present invention (I).

The modified chain aliphatic polyamine composition of the present invention (II) is a composition obtainable by addition reaction (modification) of a chain aliphatic polyamine represented by the formula (2) and an unsaturated hydrocarbon compound selected from the group consisting of a chain unsaturated hydrocarbon compound, an alicyclic unsaturated hydrocarbon compound and an aromatic unsaturated hydrocarbon compound having a carbon number of 2 to 16, preferably 2 to 10.

H₂N—(CH₂CH₂NH)ₙ—CH₂CH₂NH₂ (2)

wherein n represents a number of 0 to 4, preferably 1 to 2.

As with the present invention (I), examples of the chain aliphatic polyamine to be used in the present invention (II) include ethylenediamine, diethylenetriamine, triethylenetetramine, tetraethylenepentamine and pentaethylenehexamine, among which diethylenetriamine and triethylenetetramine are particularly preferable.

Examples of the unsaturated hydrocarbon compound to be used in the present invention (II), also as with the present invention (I), include an alkenyl compound and an alkadienyl compound such as ethylene, propylene, butene, butadiene, pentene, hexene, heptene, octene, nonene, decene, isobutylene, 2-pentene, 3-methyl-1-butene, 2-methyl-2-butene and 2,3-dimethyl-2-butene. Examples of an alicyclic unsaturated hydrocarbon compound include a cycloalkenyl compound such as cyclohexene and a cycloalkadienyl compound such as cyclohexadiene. Examples of an aromatic unsaturated hydrocarbon compound include styrene and divinylbenzene. Among these unsaturated hydrocarbon compounds, styrene is particularly preferable.

A molar number of modification of the chain aliphatic polyamine by the unsaturated hydrocarbon compound is not necessarily limited as long as gelation is avoided. However, the molar number of modification is too small, the amount of unreacted chain aliphatic polyamine becomes large, and the molar number of modification is too large, the number of active hydrogen atoms in amino groups becomes too small. Therefore, it is preferable that the relation between the molar number of modification by the unsaturated hydrocarbon compound and the number of active hydrogen atoms derived from amino groups of a chain aliphatic polyamine before modification satisfies the following mathematical formula (1).

$$\frac{A}{40} \leq X < A \quad (1)$$

wherein "A" represents a number of active hydrogen atoms in a chain aliphatic polyamine before modification and "X" represents a molar number of modification.

It is particularly preferable that the molar number of modification by an unsaturated hydrocarbon compound is selected within the range wherein the relation with a number of active hydrogen atoms derived from amino groups in a chain aliphatic polyamine before modification satisfies the following mathematical formula (2).

$$\frac{A}{16} \leq X \leq A - 2 \quad (2)$$

wherein "A" represents a number of active hydrogen atoms in a chain aliphatic polyamine before modification and "X" represents a molar number of modification.

As mentioned above, the modified chain aliphatic polyamine of the present invention (II) is obtainable by addition reaction of the chain aliphatic polyamine and the unsaturated hydrocarbon compound above-described. The reaction product after the addition reaction usually comprises at least one of the modified chain aliphatic polyamines of the present invention (I) which are addition products of the chain aliphatic polyamine and the unsaturated hydrocarbon compound, and unreacted chain aliphatic polyamine.

More specifically, the reaction product after completion of addition reaction usually comprises amino compounds such as ① an 1:1 addition product wherein 1 molecule of unsaturated hydrocarbon is added to one secondary amino group of 1 molecule of chain aliphatic polyamine, ② an 1:1 addition product wherein 1 molecule of unsaturated hydrocarbon is added to one primary amino group of 1 molecule of chain aliphatic polyamine, ③ an 1:2 addition product wherein 2 molecules of unsaturated hydrocarbon are added to one primary amino group of 1 molecule of chain aliphatic polyamine, ④ an 1:2 addition product wherein 1 molecule of unsaturated hydrocarbon is added to one primary amino group and another molecule of unsaturated hydrocarbon is added to one secondary amino group of 1 molecule of chain aliphatic polyamine, ⑤ an 1:2 addition product wherein 2 molecules of unsaturated hydrocarbon are added to each of two primary amino groups of 1 molecule of chain aliphatic polyamine respectively, ⑥ an 1:3 addition product wherein 2 molecules of unsaturated hydrocarbon are added to one primary amino group and 1 molecule of unsaturated hydrocarbon is added to one secondary amino group of 1 molecule of chain aliphatic polyamine, ⑦ an 1:3 addition product wherein 2 molecules of unsaturated hydrocarbon are added to each of two primary amino groups respectively and 1 molecule of unsaturated hydrocarbon is added to one secondary amino group of 1 molecule of chain aliphatic polyamine, ⑧ an 1:3 addition product wherein 2 molecules of unsaturated hydrocarbon are added to one primary amino group and 1 molecule of unsaturated hydrocarbon is added to another primary amino group of 1 molecule of chain aliphatic polyamine, and the like.

The content of each addition product in the reaction liquid is governed by the reaction proportion of a chain aliphatic polyamine and an unsaturated hydrocarbon compound. The higher the proportion of an unsaturated hydrocarbon compound is, the higher the proportion of the addition products having a large number of addition molecules becomes.

In the case of using diethylenetriamine as a chain aliphatic polyamine and styrene as an unsaturated hydrocarbon compound, the reaction product after completion of addition reaction comprises at least one addition product including at least one of the compounds (a) to (h) described above as a modified product in the case of 1 to 3 substituents among the substituents R1 to R5 in the formula (3) is/are a phenethyl group.

Namely, the reaction product comprises amino compounds such as

① an 1:1 addition product wherein 1 molecule of styrene is added to one secondary amino group of 1 molecule of diethylenetriamine, ② an 1:1 addition product wherein 1 molecule of styrene is added to one primary amino group of 1 molecule of diethylenetriamine, ③ an 1:2 addition product wherein 2 molecules of styrene are added to one primary amino group of 1 molecule of diethylenetriamine, ④ an 1:2 addition product wherein 1 molecule of styrene is added to one primary amino group and another molecule of styrene is added to one secondary amino group of 1 molecule of diethylenetriamine, ⑤ an 1:2 addition product wherein 2 molecules of styrene are added to each of two primary amino groups of 1 molecule of diethylenetriamine respectively, ⑥ an 1:3 addition product wherein 2 molecules of styrene are added to one primary amino group and 1 molecule of styrene is added to one secondary amino group of 1 molecule of diethylenetriamine, ⑦ an 1:3 addition product wherein 2 molecules of styrene are added to each of two primary amino groups respectively and 1 molecule of styrene is added to one secondary amino group of 1 molecule of diethylenetriamine, ⑧ an 1:3 addition product wherein 2 molecules of styrene are added to one primary amino group and 1 molecule of styrene is added to another primary amino group of 1 molecule of diethylenetriamine, and the like.

In the case that the reaction molar ratio of diethylenetriamine and styrene is 1:1, the obtainable reaction product is a mixture of at least one modified chain aliphatic polyamine described above as compounds (a) to (h) and unreacted diethylenetriamine.

A reaction liquid after completion of addition reaction generally contains unreacted chain aliphatic polyamine. The content of unreacted chain aliphatic polyamine in the modified chain aliphatic polyamine composition of the present invention (II) as a reaction product is preferably less than 2% by weight based upon the total weight of said composition.

Limiting the content of unreacted chain aliphatic polyamine under 2% by weight makes it easier to prevent the epoxy resin composition from formation of carbamate or carbonate by absorbing carbon dioxide or water vapor in the atmosphere, to avoid the phenomena of whitening or stickiness of a coating film and to prevent the coating film from deteriorating of the appearance.

When the content of unreacted chain aliphatic polyamine in the reaction product after completion of addition reaction is 2% by weight or more, it is recommended to remove the unreacted chain aliphatic polyamine by means of distillation or the like so that the content of the unreacted chain aliphatic polyamine becomes below 2% by weight. Though the method of distillation is not limited, the removal can easily be carried out by well known methods such as distillation under reduced pressure or vacuum distillation.

The viscosity of the modified chain aliphatic polyamine composition of the present invention (II) is preferably 10 to 1000 mPa·s/23° C. When the viscosity is larger than 1000 mPa·s, its workability as a curing agent for epoxy resin may be deteriorated.

The modified chain aliphatic polyamine composition of the present invention (II) has reactivity with epoxy resin and isocyanate or the like, and is useful for a curing agent for epoxy resin or a chain extender for polyurethane resin.

When a modified chain aliphatic polyamine composition of the present invention (II) is used as a curing agent for epoxy resin, it may be used independently or may be used by mixing together with other polyamine-type curing agents for epoxy resin.

In the case of using as a mixture with other curing agents, the mixing ratio of the modified chain aliphatic polyamine composition is preferably 20% by weight or more, more preferably 30% by weight or more based upon the total weight of the curing agent for epoxy resin. When the mixing ratio of the modified chain aliphatic polyamine composition is less than 20% by weight, it may cause the deterioration of the property of the epoxy resin cured product obtainable by using the curing agent for epoxy resin comprising the modified chain aliphatic polyamine composition of the present invention (II).

Preferable catalysts to be used in the process of carrying out the addition reaction in the present invention (I) and (II) include any substances exhibiting strong basicity. Examples of such catalysts include alkaline metal, alkaline metal amide and alkylated alkaline metal. Among them, alkaline metal amide by the general formula MNRR' wherein M is an alkaline metal, N is nitrogen and R and R' are, each independently, hydrogen or an alkyl group, is preferable and lithium amide ($LiNH_2$) is more preferable.

Though the amount of the catalyst depends on conditions such as species of raw material, reaction proportion and reaction temperature, it is usually 0.05 to 5% by weight and preferably 0.1 to 3% by weight based upon the total weight of a raw material.

The reaction temperature at the time of addition reaction in the present invention (I) and (II) is usually 50 to 150° C. and preferably around 80° C. When the reaction temperature is too low, the addition reaction rate may become too slow.

When the reaction temperature is too high, a polymer of unsaturated hydrocarbon compounds may be produced as a by-product.

After the completion of the reaction, the reaction liquid thus obtained comprises at least one kind of modified chain aliphatic polyamines which are addition products of a chain aliphatic polyamine and an unsaturated hydrocarbon compound, unreacted chain aliphatic polyamine and catalyst such as an alkaline metal amide.

It is possible to remove the catalyst from the reaction product by filtration. When alkaline metal amide is used as the catalyst, filtration can be easily carried out by changing the alkaline metal amide previously to a readily removable salt thereof by adding acids such as hydrochloric acid, hydrogen chloride gas and acetic acid, alcohols such as methanol and ethanol or water. For example, when water is added, alkaline metal amide is changed to hydroxide thereof which is easy to filtrate.

The filtrate obtained after removing catalyst such as alkaline metal amide or the salt thereof by filtration usually contains around 70 to 100% by weight of modified chain aliphatic polyamine and 0 to 30% by weight of unreacted aliphatic polyamine based upon the total weight of polyamine compounds.

When using the modified chain aliphatic polyamine composition wherein the content of the unreacted aliphatic polyamine is more than 30% by weight based upon the total weight of polyamine compounds as a curing agent of epoxy resin, the property of an epoxy resin cured product thus obtained may be deteriorated.

Especially, the content of unreacted chain aliphatic polyamine is preferably less than 2% by weight based upon the total weight of the modified chain aliphatic polyamine compound, as mentioned above. When the content of unreacted chain aliphatic polyamine in the reaction product after completion of addition reaction and removal of catalyst is 2% by weight or more, it is possible to remove the unreacted chain aliphatic polyamine so that the content of the unreacted chain aliphatic polyamine becomes less than 2% by weight. Though the method of removing unreacted chain aliphatic polyamine is not limited, it can be easily carried out by well known methods such as distillation. Though the method of distillation is not limited either, the removal can easily be carried out by well known methods such as distillation under reduced pressure.

A curing agent for epoxy resin of the present invention is consisting of a modified chain aliphatic polyamine of the present invention (I) and/or a modified chain aliphatic polyamine composition of the present invention (II). When using said modified chain aliphatic polyamine or said modified chain aliphatic polyamine composition as a curing agent for epoxy resin, the curing agent may be used each independently or as a mixture with other polyamine-type curing agents for epoxy resin.

The epoxy resin composition of the present invention is comprising epoxy resin and a curing agent for epoxy resin mentioned above.

Examples of epoxy resin used for an epoxy resin composition of the present invention include any epoxy resins having glycidyl groups which can react to form cross-linking bond with active hydrogen atoms derived from amino groups of the modified chain aliphatic polyamine contained in the curing agent for epoxy resin of the present invention, and any compounds can be selected from the group consisting of saturated or unsaturated aliphatic compounds, alicyclic compounds and aromatic compounds.

More specifically, examples of the epoxy resins include at least one selected from the group consisting of epoxy resin having a glycidyl ether segment derived from bisphenol A, epoxy resin having a glycidyl ether segment derived from bisphenol F, epoxy resin having a glycidyl amine segment derived from metaxylylenediamine, epoxy resin having a glycidyl amine segment derived from 1,3-bis(aminomethyl)cyclohexane, epoxy resin having a glycidyl amine segment derived from diaminodiphenylmethane, epoxy resin having a glycidyl amine segment derived from p-aminophenol, epoxy resin having a glycidyl ether segment derived from phenol novolak, and epoxy resin having a glycidyl ether segment derived from resorcinol.

Among them, epoxy resin having a glycidyl ether segment derived from bisphenol A and epoxy resin having a glycidyl ether segment derived from bisphenol F are particularly preferable.

The content of the curing agent for epoxy resin of the present invention in an epoxy resin composition is preferably the amount wherein active hydrogen equivalent of the curing agent for epoxy resin of the present invention is 0.7 to 1.0 based upon the total epoxy equivalent of epoxy resin. When the active hydrogen equivalent is less than 0.7, the degree of cross-linkage is insufficient. Meanwhile, when the active hydrogen equivalent is more than 1.0, the amount of hydrophilic amino groups becomes excessive, which causes the deterioration of water resistance.

Further, other components for modification such as filler and plasticizer, components for adjusting fluidity such as a diluent and a thixotropic agent, and other ingredients such as a pigment, a leveling agent, and a tackifier may be added to the epoxy resin composition of the present invention depending on the intended use.

The epoxy resin composition of the present invention can be cured by well known methods to obtain an epoxy resin cured product. The curing condition is not limited and it can be selected appropriately depending on the intended use.

PREFERRED EMBODIMENT OF THE INVENTION

The present invention will be described in more detail below, referring to Examples which are not intended to limit the scope of the present invention. Analysis of a modified chain aliphatic polyamine and evaluation of the property of an epoxy resin coating film are carried out by the following methods.

[Analysis of a Modified Chain Aliphatic Polyamine]

(1) Gas Chromatography Analysis

Column: "CP-CIL8CB" manufactured by CHROMPACK Co.; length 30 m, film thickness 2.5 μm, inner diameter 0.25 mm.

Column temperature: 120° C./10 minutes+elevation of temperature at the rate of 10° C./minute+300° C./60 minutes.

(2) Nuclear Magnetic Resonance (NMR) Absorption Method ($^1$H-NMR, $^{13}$C-NMR)

"JNM-AL400" type Nuclear Magnetic Resonance Apparatus, manufactured by Japan Electron Optics Laboratory Ltd., in Japan was used.

"σ(ppm)" after-mentioned indicates a chemical shift represented by the following formula:

$$\sigma(ppm) = 10^6 \times (v_1 - v_2)/v_2$$

$v_1$: resonance frequency (Hz) of a sample v$_2$: resonance frequency (Hz) of trimethylsilane (TMS) as a standard substance

[Evaluation of Property of Epoxy Resin Coating Film]

An epoxy resin composition was coated on a steel plate with thickness of 200 μm under the conditions of 23° C. and 50% RH.

a) Appearance:

The appearance of a coating film after 7 days of curing was evaluated visually (gloss, clarity, leveling), and by touching with finger (dryness).

b) Water Resistance:

Water droplets were placed on a coating film after 1, 4, and 7 days of curing. After 24 hours, water on the coating film was wiped up and the condition of the coating film was evaluated visually.

c) Chemical Resistance:

Coated steel plates after 7 days of curing were dipped in each chemicals (sodium hydroxide with the concentration of 10%, sulfuric acid with the concentration of 10%, acetic acid with the concentration of 10%, methanol and toluene) for 7 days under the condition of 23° C. Change of the appearance of the coating films were evaluated visually.

d) Salt Spray Resistance

Salt spray test was carried out based on JIS K 5400. Change of the appearance of the coating film after 7 days of spraying was evaluated visually.

<Evaluation>

Evaluation was carried out based on the following 4 stages of criteria.

⊚; Excellent, ○; good Δ; fair X; poor

EXAMPLE 1

412.7 g (4.0 mol) of diethylenetriamine, a special grade reagent manufactured by Kanto Kagaku Co., in Japan (hereinafter, "DETA") having the number of active hydrogen atoms of 5 and 2.5 g (0.11 mol; 0.3% by weight) of lithium amide, a reagent manufactured by Merck Ltd., were charged to a 2 L (liter) flask equipped with an agitator, a thermometer, a nitrogen gas inlet, a dropping funnel and a condenser. Then, its interior temperature was raised to 80° C. in a nitrogen gas stream with stirring. Keeping the temperature at 80° C., 416.8 g (4.0 mol) of styrene, a special grade reagent, manufactured by Wako Pure Chemical Industries, Ltd., in Japan was added thereto dropwise over 2 hours. After the completion of dropwise addition, its interior temperature was maintained to 80° C. for 0.5 hours.

Then, after the reaction liquid was cooled to the room temperature, 19.8 g (1.1 mol) of water as the amount of 10 times equal mol to the charged lithium amide was added thereto and stirred. After separating precipitates in the liquid in flask by filtration, remained water was removed by vacuum distillation, whereby 777.0 g of Polyamine(1) was obtained as a reaction product. The molar number of modification of the Polyamine(1) was 1.0 mole and the viscosity thereof was 22 mPa·s/25° C. The content of unreacted DETA in the Polyamine(1) was 16.3% by weight. The active hydrogen equivalent was 52.

As the result of GC analysis of the Polyamine(1) thus obtained, 8 peaks other than the peak of unreacted DETA were detected. When the 8 peaks were assumed as peaks a, b, c, d, e, f, g, and h in the order of retention time, the peak area ratio was DETA: 11.9%, peak a: 8.0%, peak b: 31.2%, peak c: 8.2%, peak d: 20.7%, peak e: 10.2%, peak f: 2.5%, peak g: 4.2%, peak h: 3.0%. (See FIG. 1).

Figure 2:
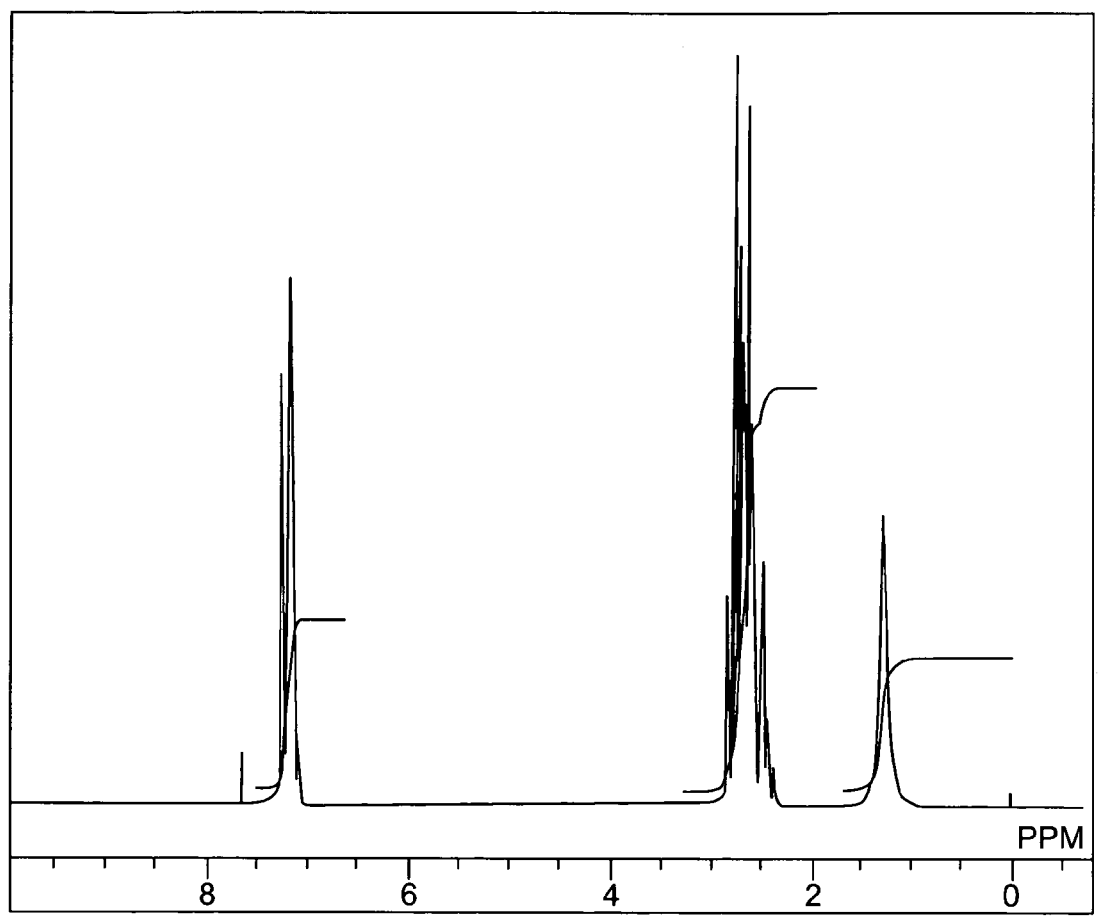
FIG. 2 is a $^1$H-NMR spectrum of polyamine(1) synthesized in Example 1.

$^1$H-NMR measurement was carried out for the Polyamine (1) obtained above. $^1$H-NMR spectrum of the Polyamine(1) was shown in FIG. 2.

From the result of $^1$H-NMR measurement, 4.0 ppm(4H, s, —NH$_2$, —NH—), 2.5-2.8 ppm(12H, m, —CH$_2$—), 7.1-7.3 ppm(5H, m, Ar) were detected. Thus, it was confirmed that each of the peaks a to h was a product obtained by addition reaction of DETA and styrene.

Figure 3:
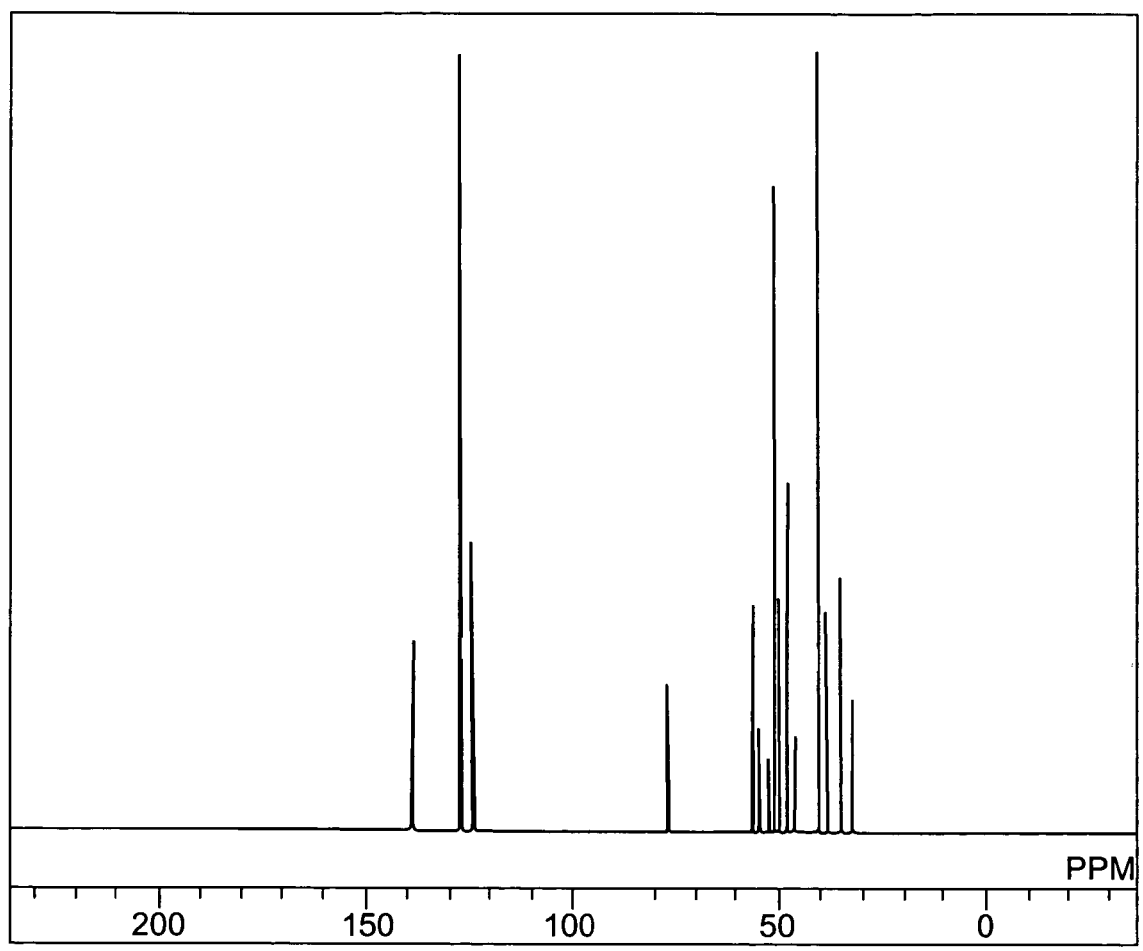
FIG. 3 is a $^{13}$C-NMR spectrum of polyamine(1) synthesized in Example 1.

$^{13}$C-NMR measurement was carried out for the Polyamine (1) obtained above. $^{13}$C-NMR spectrum of the Polyamine(1) was shown in FIG. 3.

From the result of $^{13}$C-NMR measurement, each chemical species of the peaks a to h was identified.

The spectrum derived from the peak a was as follows, whereby the chemical species of the peak a was identified as a compound (a) described above:

$^1$H-NMR σ[ppm]; 1.3 ppm(4H, s, —NH$_2$), 2.5-2.8 ppm (12H, m, —CH$_2$—), 7.1-7.3 ppm(5H, m, Ar), $^{13}$C-NMR σ[ppm]; 38.8 ppm(H$_2$N—CH$_2$—CH$_2$—N=), 56.1 ppm(H$_2$N—CH$_2$—CH$_2$—N=), 32.7 ppm(Ar—CH$_2$—CH$_2$—), 55.0 ppm(Ar—CH$_2$—CH$_2$—), 124.6 ppm(Ar), 127.0 ppm(Ar), 127.4 ppm(Ar), 139.3 ppm(Ar).

The spectrum derived from the peak b was as follows, whereby the chemical species of the peak b was identified as a compound (b) described above:

$^1$H-NMR σ[ppm]; 1.3 ppm(4H, s, —NH$_2$—NH—), 2.5-2.8 ppm(12H, m, —CH$_2$—), 7.1-7.3 ppm(5H, m, Ar), $^{13}$C-NMR σ[ppm]; 40.8 ppm(H$_2$N—CH$_2$—CH$_2$—NH—), 51.4 ppm(H$_2$N—CH$_2$—CH$_2$—NH—), 48.1 ppm (—NH—CH$_2$—CH$_2$—NH—CH$_2$—CH$_2$—Ar), 50.1 ppm (—NH—CH$_2$—CH$_2$—NH—CH$_2$—CH$_2$—Ar), 35.4 ppm(Ar—CH$_2$—CH$_2$—), 48.2 ppm(Ar—CH$_2$—CH$_2$—), 124.7 ppm(Ar), 127.1 ppm(Ar), 127.4 ppm(Ar), 138.9 ppm(Ar).

The spectrum derived from the peak c was as follows, whereby the chemical species of the peak c was identified as a compound (c) described above:

$^1$H-NMRσ [ppm]; 1.3 ppm(3H, s, —NH$_2$, —NH—), 2.5-2.8 ppm(16H, m, —CH$_2$—), 7.1-7.3 ppm(10H, m, Ar), $^{13}$C-NMR σ[ppm]; 40.9 ppm(H$_2$N—CH$_2$—CH$_2$—NH—), 51.4 ppm(H$_2$N—CH$_2$—CH$_2$—NH—), 52.9 ppm (—NH—CH$_2$—CH$_2$—N—(CH$_2$—CH$_2$—Ar)$_2$), 50.3 ppm (—NH—CH$_2$—CH$_2$—N—(CH$_2$—CH$_2$—Ar)$_2$), 32.7 ppm(Ar—CH$_2$—CH$_2$—), 55.1 ppm(Ar—CH$_2$—CH$_2$—), 124.5 ppm(Ar), 126.9 ppm(Ar), 127.5 ppm(Ar), 139.4 ppm(Ar).

The spectrum derived from the peak d was as follows, whereby the chemical species of the peak d was identified as a compound (d) described above:

$^1$H-NMR σ[ppm]; 1.3 ppm(3H, s, —NH$_2$, —NH—), 2.5-2.8 ppm(16H, m, —CH$_2$—), 7.1-7.3 ppm(10H, m, Ar), $^{13}$C-NMR σ[ppm]; 38.8 ppm(H$_2$N—CH$_2$—CH$_2$—N=), 56.1 ppm(H$_2$N—CH$_2$—CH$_2$—N=), 54.7 ppm (=N—CH$_2$—CH$_2$—NH—CH$_2$—CH$_2$—Ar), 46.5 ppm (=N—CH$_2$—CH$_2$—NH—CH$_2$—CH$_2$—Ar), 32.7 ppm(Ar—CH$_2$—CH$_2$—N=), 55.0 ppm(Ar—CH$_2$—CH$_2$—N=), 35.4 ppm(Ar—CH$_2$—CH$_2$—NH—), 48.2 ppm(Ar—CH$_2$—CH$_2$—NH—), 124.6 ppm(Ar), 124.7 ppm(Ar), 127.0 ppm(Ar), 127.1 ppm(Ar), 127.4 ppm(Ar), 138.9 ppm(Ar), 139.3 ppm(Ar).

The spectrum derived from the peak e was as follows, whereby the chemical species of the peak e was identified as a compound (e) described above:

$^1$H-NMR σ[ppm]; 1.3 ppm(3H, s, —NH—), 2.5-2.8 ppm (16H, m, —CH$_2$—), 7.1-7.3 ppm(10H, m, Ar), $^{13}$C-NMR σ[ppm]; 48.1 ppm(—NH—CH$_2$—CH$_2$—NH—CH$_2$—CH$_2$—Ar), 50.3 ppm(—NH—CH$_2$—CH$_2$—NH—CH$_2$—CH$_2$—Ar), 35.4 ppm(Ar—CH$_2$—CH$_2$—), 48.2 ppm(Ar—CH$_2$—CH$_2$—), 124.7 ppm(Ar), 127.1 ppm(Ar), 127.4 ppm(Ar), 138.9 ppm(Ar).

The spectrum derived from the peak f was as follows, whereby the chemical species of the peak f was identified as a compound (f) described above:

$^1$H-NMR σ[ppm]; 1.3 ppm(2H, s, —NH—), 2.5-2.8 ppm (20H, m, —CH$_2$—), 7.1-7.3 ppm(15H, m, Ar), $^{13}$C-NMR σ[ppm]; 38.9 ppm(H$_2$N—CH$_2$—CH$_2$—N═), 56.1 ppm(H$_2$N—CH$_2$—CH$_2$—N═), 51.9 ppm (═N—CH$_2$—CH$_2$—N—(CH$_2$—CH$_2$—Ar)$_2$), 52.5 ppm (═N—CH$_2$—CH$_2$—N—(CH$_2$—CH$_2$—Ar)$_2$), 35.6 ppm(Ar—CH$_2$—CH$_2$—N═), 48.4 ppm(Ar—CH$_2$—CH$_2$—N═), 32.9 ppm((Ar—CH$_2$—CH$_2$)$_2$—N—), 54.8 ppm((Ar—CH$_2$—CH$_2$)$_2$—N—), 124.5 ppm(Ar), 124.6 ppm(Ar), 126.9 ppm(Ar), 127.0 ppm(Ar), 127.4 ppm(Ar), 127.5 ppm(Ar), 139.3 ppm(Ar), 139.4 ppm(Ar).

The spectrum derived from the peak g was as follows, whereby the chemical species of the peak g was identified as a compound (g) described above:

$^1$H-NMR σ[ppm]; 1.3 ppm(2H, s, —NH—), 2.5-2.8 ppm (20H, m, —CH$_2$—), 7.1-7.3 ppm(15H, m, Ar), $^{13}$C-NMR σ[ppm]; 54.7 ppm(═N—CH$_2$—CH$_2$—NH—CH$_2$—CH$_2$—Ar), 46.4 ppm(═N—CH$_2$—CH$_2$—NH—CH$_2$—CH$_2$—Ar), 32.8 ppm (Ar—CH$_2$—CH$_2$—NH—), 54.8 ppm(Ar—CH$_2$—CH$_2$—NH—), 35.5 ppm(Ar—CH$_2$—CH$_2$—N═), 48.2 ppm(Ar—CH$_2$—CH$_2$—N═), 124.6 ppm(Ar), 124.7 ppm(Ar), 127.0 ppm(Ar), 127.1 ppm(Ar), 127.4 ppm(Ar), 138.9 ppm(Ar), 139.3 ppm(Ar).

The spectrum derived from the peak h was as follows, whereby the chemical species of the peak h was identified as a compound (h) described above:

$^1$H-NMR σ[ppm]; 1.3 ppm(2H, s, —NH—), 2.5-2.8 ppm (20H, m, —CH$_2$—), 7.1-7.3 ppm(15H, m, Ar), $^{13}$C-NMR σ[ppm]; 52.9 ppm(—NH—CH$_2$—CH$_2$—N—(CH$_2$—CH$_2$—Ar)$_2$), 50.4 ppm(—NH—CH$_2$—CH$_2$—N— (CH$_2$—CH$_2$—Ar)$_2$), 48.1 ppm (—NH—CH$_2$—CH$_2$—NH—CH$_2$—CH$_2$—Ar), 50.1 ppm (—NH—CH$_2$—CH$_2$—NH—CH$_2$—CH$_2$—Ar), 32.7 ppm (Ar—CH$_2$—CH$_2$—NH—), 55.0 ppm(Ar—CH$_2$—CH$_2$—NH—), 32.7 ppm((Ar—CH$_2$—CH$_2$)$_2$—N—), 55.1 ppm((Ar—CH$_2$—CH$_2$)$_2$—N—), 124.5 ppm(Ar), 124.7 ppm(Ar), 126.9 ppm(Ar), 127.1 ppm(Ar), 127.4 ppm(Ar), 127.5 ppm(Ar), 138.9 ppm(Ar), 139.4 ppm(Ar).

An epoxy resin composition was prepared by mixing bisphenol A type liquid epoxy resin with an epoxy equivalent of 190 g/eq, manufactured by Japan Epoxy Resins Co., Ltd., trade name; Epicoat 828, and the above Polyamine(1) as a curing agent for epoxy resin at a ratio shown in Table 1.

The epoxy resin composition thus obtained was cured under the conditions of 23° C. and 50% RH to prepare an epoxy resin cured coating film, and the property of the coating film was evaluated. The evaluation result was shown in Table 1.

EXAMPLE 2

584.8 g (4.0 mol) of triethylenetetramine, a special grade reagent manufactured by Kanto Kagaku Co., in Japan (hereinafter, "TETA") having the number of active hydrogen atoms of 6 and 3.0 g (0.13 mol; 0.3% by weight) of lithium amide were charged to a flask similar as the one used in Example 1. Then the reaction was carried out in the same manner as Example 1.

Then, after the reaction liquid was cooled to the room temperature, 23.4 g (1.3 mol) of water as the amount of 10 times equal mol to the charged lithium amide was added thereto and stirred. After separating precipitates in the liquid in flask by filtration, remained water was removed by vacuum distillation, whereby 990 g of Polyamine(2) was obtained as a reaction product. The molar number of modification of the Polyamine(2) was 1.0 mole and the viscosity thereof was 77 mPa·s/25° C. The content of unreacted TETA in the Polyamine(2) was 17.0% by weight. The active hydrogen equivalent was 50.

An epoxy resin composition was prepared by mixing bisphenol A type liquid epoxy resin with an epoxy equivalent of 190 g/eq, manufactured by Japan Epoxy Resins Co., Ltd., trade name; Epicoat 828, and the Polyamine(2) as a curing agent for epoxy resin at a ratio shown in Table 1.

The epoxy resin composition thus obtained was cured under the conditions of 23° C. and 50% RH to prepare an epoxy resin cured coating film, and the property of the coating film was evaluated. The evaluation result was shown in Table 1.

EXAMPLE 3

412.7 g (4.0 mol) of DETA and 2.5 g (0.11 mol; 0.3% by weight) of lithium amide were charged to a 2 L (liter) flask equipped with an agitator, a thermometer, a nitrogen gas inlet, a dropping funnel and a condenser. Then, its interior temperature was raised to 80° C. in a nitrogen gas stream with stirring. Keeping the temperature at 80° C., 416.8 g (4.0 mol) of styrene, a special grade reagent, manufactured by Wako Pure Chemical Industries, Ltd., in Japan was added thereto dropwise over 2 hours. After the completion of dropwise addition, its interior temperature was maintained to 80° C. for 0.5 hours.

Then, after the reaction liquid was cooled to the room temperature, 19.8 g (1.1 mol) of water as the amount of 10 times equal mol to the charged lithium amide was added thereto and stirred. After separating precipitates in the liquid in flask by filtration, remained water and unreacted DETA were removed by vacuum distillation, whereby 640.3 g of Polyamine(3) was obtained as a reaction product. The molar number of modification of the Polyamine(3) was 1.5 mol and the viscosity thereof was 35 mPa·s/25° C. The content of unreacted DETA in the Polyamine(3) was 0.2% by weight. The active hydrogen equivalent was 75.

An epoxy resin composition was prepared by mixing bisphenol A type liquid epoxy resin with an epoxy equivalent of 190 g/eq, manufactured by Japan Epoxy Resins Co., Ltd., trade name; Epicoat 828, and the Polyamine(3) as a curing agent for epoxy resin at a ratio shown in Table 1.

The epoxy resin composition thus obtained was cured under the conditions of 23° C. and 50% RH to prepare an epoxy resin cured coating film, and the property of the coating film was evaluated. The evaluation result was shown in Table 1.

EXAMPLE 4

584.8 g (4.0 mol) of TETA and 3.0 g (0.13 mol; 0.3% by weight) of lithium amide were charged to a flask similar as the one used in Example 1. Then, its interior temperature was raised to 80° C. in a nitrogen gas stream with stirring. Keeping the temperature at 80° C., 416.8 g (4.0 mol) of styrene, a special grade reagent, manufactured by Wako Pure Chemical Industries, Ltd., in Japan was added thereto dropwise over 2 hours. After the completion of dropwise addition, its interior temperature was maintained to 80° C. for 0.5 hours.

Then, after the reaction liquid was cooled to the room temperature, 23.4 g (1.3 mol) of water as the amount of 10 times equal mol to the charged lithium amide was added thereto and stirred. After separating precipitates in the liquid in flask by filtration, remained water and unreacted TETA were removed by vacuum distillation, whereby 802 g of Polyamine(4) was obtained as a reaction product. The molar number of modification of the Polyamine(4) was 1.4 mol and the viscosity thereof was 116 mPa·s/25° C. The content of unreacted TETA in the Polyamine(4) was 0.3% by weight. The active hydrogen equivalent was 68.

An epoxy resin composition was prepared by mixing bisphenol A type liquid epoxy resin with an epoxy equivalent of 190 g/eq, manufactured by Japan Epoxy Resins Co., Ltd., trade name; Epicoat 828, and the Polyamine(4) as a curing agent for epoxy resin at a ratio shown in Table 1.

The epoxy resin composition thus obtained was cured under the conditions of 23° C. and 50% RH to prepare an epoxy resin cured coating film, and the property of the coating film was evaluated. The evaluation result was shown in Table 1.

COMPARATIVE EXAMPLE 1

In the Comparative Example 1, a Mannich modification was employed as one of the examples of modification without using unsaturated hydrocarbon compounds.

141 g (1.50 mol) of phenol, a special grade reagent manufactured by Kanto Kagaku Co., in Japan, 81 g of formalin manufactured by Mitsubishi Gas Chemical Co., Inc., in Japan containing 37% by weight of formaldehyde and 4 g (0.04 mol) of DETA were charged to a 2 L (liter) flask equipped with an agitator, a thermometer, a nitrogen gas inlet, a dropping funnel and a condenser. Then, its interior temperature was raised to 100° C. in a nitrogen gas stream with stirring.

After stirring for 1 hour with keeping the temperature at 100° C., 151 g (1.47 mol) of DETA was added thereto and the reaction was carried out for 1 hour under the temperature of 100° C. Then, the temperature was raised to 170° C. over 2.5 hours with removing water, whereby 300 g of DETA Mannich reaction product was obtained.

The viscosity of the DETA Mannich reaction product was 5400 mPa·s/25° C. The content of unreacted DETA in the DETA Mannich reaction product was 36.3% by weight. The active hydrogen equivalent was 40.

An epoxy resin composition was prepared by mixing bisphenol A type liquid epoxy resin and the DETA Mannich reaction product as a curing agent for epoxy resin at a ratio shown in Table 2.

The epoxy resin composition thus obtained was cured under the conditions of 23° C. and 50% RH to prepare an epoxy resin cured coating film, and the property of the coating film was evaluated. The evaluation result was shown in Table 2.

COMPARATIVE EXAMPLE 2

In the Comparative Example 2, a Mannich modification was employed as one of the examples of modification without using unsaturated hydrocarbon compounds.

212 g (2.25 mol) of phenol, 122 g of formalin containing 37% by weight of formaldehyde and 8 g (0.05 mol) of TETA were charged to a 2 L (liter) flask equipped with an agitator, a thermometer, a nitrogen gas inlet, a dropping funnel and a condenser. Then, its interior temperature was raised to 100° C. in a nitrogen gas stream with stirring.

After stirring for 1 hour with keeping the temperature at 100° C., 321 g (2.20 mol) of TETA was added thereto and the reaction was carried out for 1 hour under the temperature of 100° C. Then, the temperature was raised to 170° C. over 2.5 hours with removing water, whereby 560 g of TETA Mannich reaction product was obtained.

The viscosity of the TETA Mannich reaction product was 6900 mPa·s/25° C. The content of unreacted TETA in the TETA Mannich reaction product was 38.3% by weight. The active hydrogen equivalent was 70.

An epoxy resin composition was prepared by mixing bisphenol A type liquid epoxy resin and the TETA Mannich reaction product as a curing agent for epoxy resin at a ratio shown in Table 2.

The epoxy resin composition thus obtained was cured under the conditions of 23° C. and 50% RH to prepare an epoxy resin cured coating film, and the property of the coating film was evaluated. The evaluation result was shown in Table 2.

TABLE 1

|  | Example 1 | Example 2 | Example 3 | Example 4 |
|---|---|---|---|---|
| Epoxy resin composition (g) | | | | |
| Epicoat 828 | 100 | 100 | 100 | 100 |
| Polyamine (1) | 28 | | | |
| Polyamine (2) | | 26 | | |
| Polyamine (3) | | | 40 | |
| Polyamine (4) | | | | 36 |
| Property of a cured coating film | | | | |
| Appearance | | | | |
| Gloss | ◎ | ◎ | ◎ | ◎ |
| Clarity | ○ | ○ | ◎ | ◎ |
| leveling | ○ | ○ | ◎ | ◎ |
| Drying characteristics | ○ | ○ | ◎ | ◎ |
| Water resistance | | | | |
| (1/4/7days) | △/○/◎ | △/○/◎ | ◎/◎/◎ | ◎/◎/◎ |
| Chemical resistance | | | | |
| 10% sodium hydroxide | △ | △ | △ | △ |
| 10% sulfuric acid | △ | △ | ○ | ○ |
| 10% acetic acid | △ | △ | △ | △ |
| methanol | ○ | ○ | ○ | ○ |
| toluene | ○ | ○ | ○ | ○ |
| Solt Spray Resistance | ○ | ○ | ○ | ○ |

TABLE 2

|  | Comparative Example 1 | Comparative |
|---|---|---|
| Epoxy resin composition (g) | | |
| Epicoat 828 | 100 | 100 |
| DETA Mannich Reaction Product | 21 | |
| TETA Mannich Reaction Product | | 37 |
| Property of a cured coating film | | |
| Appearance | | |
| Gloss | △ | △ |
| Clarity | △ | △ |
| leveling | △ | △ |
| Drying characteristics | X | X |
| Water resistance | | |
| (1/4/7days) | X/△/○ | X/△/○ |

TABLE 2-continued

|  | Comparative Example 1 | Comparative |
| --- | --- | --- |
| Chemical resistance |  |  |
| 10% sodium hydroxide | Δ | Δ |
| 10% sulfuric acid | X | Δ |
| 10% acetic acid | X | X |
| methanol | Δ | Δ |
| toluene | ○ | X |
| Solt Spray Resistance | X | X |

As clear from the above Examples, a modified chain aliphatic polyamine of the present invention (I) has a low viscosity and the content of unreacted chain aliphatic polyamine is relatively small. Thus, the epoxy resin composition comprising the above modified chain aliphatic polyamine as a curing agent for epoxy resin provides an epoxy resin cured product having excellent properties.

Moreover, a modified chain aliphatic polyamine composition of the present invention (II) wherein the content of unreacted chain aliphatic polyamine is less than 2% by weight based on the total weight of the composition provides, when used as a curing agent for epoxy resin, an epoxy resin cured product having excellent properties especially in the appearance of a coating film, water resistance and chemical resistance.

In particular, an epoxy resin composition comprising a new chemical compound of modified chain aliphatic polyamine obtained by addition reaction of diethylenetriamine and styrene provides an epoxy resin cured product having excellent properties.

What is claimed is:

1. A modified chain aliphatic polyamine composition obtained by addition reaction of a chain aliphatic polyamine represented by the following formula (2):

$$H_2N-(CH_2CH_2NH)_n-CH_2CH_2NH_2 \quad (2)$$

wherein "n" represents a number of 0 to 4, and an unsaturated hydrocarbon compound selected from the group consisting of styrene and divinylbenzene, which composition comprises a first modified chain aliphatic polyamine represented by the following formula (1):

$$R1R2N-(CH_2CH_2NR3)_n-CH_2CH_2NR4R5 \quad (1)$$

wherein each of substituents R1, R2, R3, R4 and R5 represents independently a hydrogen atom or an unsaturated hydrocarbon residue selected from the group consisting of styrene residue and divinylbenzene residue, one of R1, R2, R3, R4 and R5 is an unsaturated hydrocarbon residue selected from the group consisting of styrene residue and divinylbeuzene residue, and a second modified chain aliphatic polyamine represented by the following formula (1):

$$R1R2N-(CH_2CH_2NR3)_n-CH_2CH_2NR4R5 \quad (1)$$

wherein each of substituents R1, R2, R3, R4 and R5 represents independently a hydrogen atom or an unsaturated hydrocarbon residue selected from the group consisting of styrene residue and divinylbenzene residue, one of R1, R2, R3, R4 and R5 is an unsaturated hydrocarbon residue selected from the group consisting of styrene residue and divinylbenzene residue, and "n" represents a number of 1 to 4.

2. The modified chain aliphatic polyamine composition according to claim 1, wherein said chain aliphatic polyamine is diethylenetriamine andlor triethylenetetramine.

3. The modified chain aliphatic polyamine composition according to claim 1, wherein said unsaturated hydrocarbon compound is styrene.

4. The modified chain aliphatic polyamine composition according to claim 2, wherein said unsaturated hydrocarbon compound is styrene.

5. The modified chain aliphatic polyamine composition according to claim 1, wherein a molar number of modification of said chain aliphatic polyamine by said unsaturated hydrocarbon compound satisfies the following mathematical formula (1):

$$\frac{A}{40} \leq X < A \quad (1)$$

wherein "A" represents a number of active hydrogen atoms in said chain aliphatic polyamine and "X" represents a molar number of modification.

6. The modified chain aliphatic polyamine composition according to claim 1, wherein the content of unreacted chain aliphatic polyamine is less than 2% by weight based upon the total weight of said modified chain aliphatic polyamine composition.

7. A curing agent for epoxy resin comprising the modified chain aliphatic polyamine composition according to claim 1.

8. An epoxy resin composition comprising epoxy resin and the curing agent for epoxy resin according to claim 7.

9. An epoxy resin cured product obtained by curing the epoxy resin composition according to claim 8.

* * * * *